United States Patent
Takahashi (10) Patent No.: US 10,398,913 B2
(45) Date of Patent: Sep. 3, 2019

(54) CONTROL DEVICE FOR TREATMENT PLANNING APPARATUS, CONTROL METHOD, AND PROGRAM

(71) Applicant: HITACHI, LTD., Tokyo (JP)

(72) Inventor: Kunio Takahashi, Tokyo (JP)

(73) Assignee: HITACHI, LTD., Tokyo (JP)

( * ) Notice: Subject to any disclaimer, the term of this patent is extended or adjusted under 35 U.S.C. 154(b) by 481 days.

(21) Appl. No.: 15/030,867

(22) PCT Filed: Oct. 24, 2013

(86) PCT No.: PCT/JP2013/078874
§ 371 (c)(1),
(2) Date: Jun. 1, 2016

(87) PCT Pub. No.: WO2015/059805
PCT Pub. Date: Apr. 30, 2015

(65) Prior Publication Data
US 2016/0271423 A1      Sep. 22, 2016

(51) Int. Cl.
*A61N 5/10*      (2006.01)

(52) U.S. Cl.
CPC .......... *A61N 5/1049* (2013.01); *A61N 5/103* (2013.01); *A61N 5/1037* (2013.01); *A61N 5/1045* (2013.01); *A61N 5/1069* (2013.01); *A61N 2005/1059* (2013.01); *A61N 2005/1087* (2013.01)

(58) Field of Classification Search
CPC ................ A61N 5/1037; A61N 5/1049; A61N 2005/1051; A61N 2005/1056; A61N 2005/10059; A61N 2005/1061

USPC ................................................ 600/1; 378/65
See application file for complete search history.

(56) References Cited

U.S. PATENT DOCUMENTS

| | | |
|---|---|---|
| 2006/0100509 A1 | 5/2006 | Wright et al. |
| 2010/0054412 A1 | 3/2010 | Brinks et al. |
| 2010/0198101 A1 | 8/2010 | Song et al. |

(Continued)

FOREIGN PATENT DOCUMENTS

| | | |
|---|---|---|
| JP | 2007-507275 A | 3/2007 |
| JP | 2010-183976 A | 8/2010 |

OTHER PUBLICATIONS

International Search Report in International Application No. PCT/JP2013/078874, dated Jan. 28, 2014.

(Continued)

*Primary Examiner* — Samuel G Gilbert (57) ABSTRACT

Provided is a control device for a radiation irradiation device including a position-related information acquisition portion that acquires position-related information related to a position of a particular site; a model generation portion that generates a model outputting the position of the particular site based on the position-related information; and a particular site position calculation portion that outputs the position of the particular site based on the position-related information acquired by the position-related information acquisition portion, by using the model generated by the model generation portion. The model generated by the model generation portion is provided with a filter regulating an amount of change in the position of the particular site output by the model.

7 Claims, 9 Drawing Sheets

(56) References Cited

U.S. PATENT DOCUMENTS

2013/0006036 A1    1/2013  Raleigh et al.
2014/0107390 A1*   4/2014  Brown ................ A61N 5/1045
                                                                 600/1

OTHER PUBLICATIONS

International Preliminary Report on Patentability in International Application No. PCT/JP2013/078874, dated Feb. 2, 2016.
Gregory C Sharp et al, "Prediction of respiratory tumour motion for real-time image-guided radiotherapy; Prediction of respiratory tumour motion", Physics in Medicine and Biology, Institute of Physics Publishing, Bristol GB, vol. 49, No. 3, Feb. 7, 2004 (Feb. 7, 2004), pp. 425-440.
Olivier C L Haas et al, "Paper; Couch-based motion compensation: modelling, simulation and real-time experiments; Couch-based motion compensation: modelling, simulation and real-time experiments", Physics in Medicine and Biology, Institute of Physics Publishing, Bristol GB, vol. 57, No. 18, Sep. 5, 2012 (Sep. 5, 2012), pp. 5787-5807.
Extended European Search Report in EP Application No. 13896186.7, dated Dec. 20, 2016.

* cited by examiner

CONTROL DEVICE FOR TREATMENT PLANNING APPARATUS, CONTROL METHOD, AND PROGRAM

RELATED APPLICATIONS

The present application is a National Phase entry of International Application No. PCT/JP2013/078874, filed Oct. 24, 2013.

TECHNICAL FIELD

The present invention relates to controlling of a treatment planning apparatus, a control method, and a program.

BACKGROUND ART

As a method of controlling a radiation treatment apparatus, tracking irradiation has been proposed and practically applied (for example, Patent Document 1). The aforementioned tracking irradiation is a method in which positional information on a particular site (a tumor or the like) moving due to breathing and the like is acquired in real time and the radiation treatment apparatus is controlled such that the radiation treatment apparatus continuously irradiates the particular site with radiation. As the radiation treatment apparatus intensively irradiates the particular site with radiation through tracking irradiation, it is possible to ensure a radiation dosage at the particular site and to reduce the radiation dosage at surrounding sites.

As a method of acquiring positional information on a particular site when performing tracking irradiation, there is a method of detecting a position of a marker provided on a body surface or inside a body and calculating the positional information on the particular site from positional information on the marker.

PRIOR ART DOCUMENTS

Patent Document

[Patent Document 1] Japanese Unexamined Patent Application, First Publication No. 2010-183976

SUMMARY OF THE INVENTION

Problem to be Solved by the Invention

As in a method of calculating positional information on a particular site from positional information on a marker, in a method of acquiring the positional information on the particular site based on other types of information, accuracy in the acquired positional information on the particular site is important in order to enhance the accuracy when irradiating the particular site with radiation.

The present invention provides a control device for a treatment planning apparatus, a control method, and a program, in which positional information on the particular site can be acquired with highly improved accuracy.

Means for Solving the Problem

A control device for a radiation treatment apparatus according to a first aspect of the present invention includes: a position-related information acquisition portion that acquires position-related information related to a position of a particular site; a model generation portion that generates a model outputting the position of the particular site based on the position-related information; and a particular site position calculation portion that outputs the position of the particular site based on the position-related information acquired by the position-related information acquisition portion, by using the model generated by the model generation portion. The model generated by the model generation portion is provided with a filter regulating an amount of change in the position of the particular site output by the model, and the model generation portion sets parameters of a model template provided with the filter so as to minimize an error between an output after passing through the filter and the teacher signal indicating the correct decision of the position of the particular site, to generate the model provided with the filter.

The model generation portion may generate a plurality of the models in each of which the filter is provided at a position different from that in each of the others and may select any one of the models. The particular site calculation portion may output the position of the particular site based on the position-related information acquired by the position-related information acquisition portion, by using the model selected by the model generation portion.

A control method according to a second aspect of the present invention is a control method for controlling the radiation treatment apparatus by a control device for a radiation treatment apparatus. The control method includes a position-related information acquisition portion step of acquiring position-related information related to a position of a particular site; a model generation step of generating a model outputting the position of the particular site based on the position-related information; and a particular site position calculation step of outputting the position of the particular site based on the position-related information acquired in the position-related information acquisition step, by using the model generated in the model generation step. The model generated in the model generation step is provided with a filter regulating an amount of change in the position of the particular site output by the model; and in the model generation step, parameters of a model template provided with the filter are set so as to minimize an error between an output after passing through the filter and the teacher signal indicating the correct decision of the position of the particular site, to generate the model provided with the filter A program according to a third aspect of the present invention causes a computer including a control device for a radiation treatment apparatus to execute: a position-related information acquisition portion step of acquiring position-related information related to a position of a particular site; and a model generation step of generating a model outputting the position of the particular site based on the position-related information; and a particular site position calculation step of outputting the position of the particular site based on the position-related information acquired in the position-related information acquisition step, by using the model generated in the model generation step. In the model generation step, parameters of a model template provided with the filter are set so as to minimize an error between an output after passing through the filter, the filter regulating an amount of change in the position of the particular site output by the model, and the teacher signal indicating the correct decision of the position of the particular site, to generate the model provided with the filter, and the model provided with the filter is generated.

Effect of the Invention

According to the controlling of a treatment planning apparatus, the control method, and the program described

EMBODIMENTS FOR CARRYING OUT THE INVENTION

Hereinafter, while an embodiment of the present invention will be described, the following embodiment does not limit the present invention applied to the accompanying claims. In addition, all of the combinations of features described in the embodiment are not necessarily indispensable for the solution to the problem of the present invention.

Figure 1:
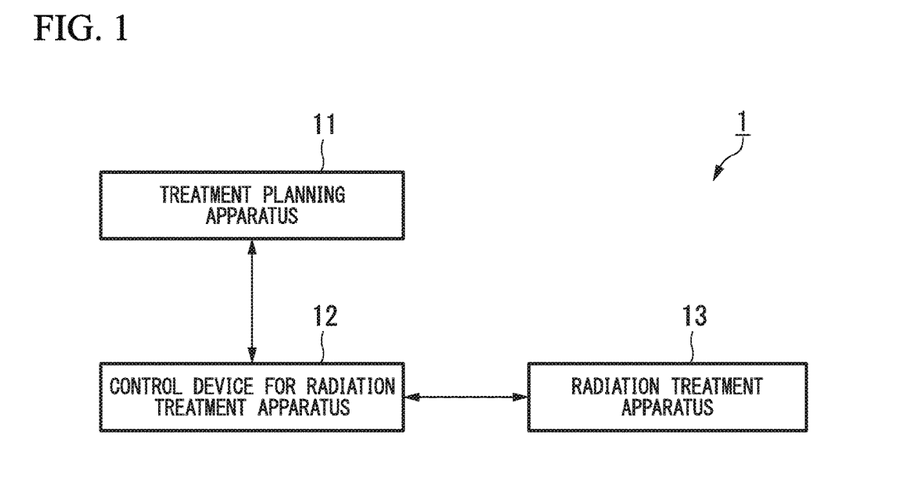
FIG. 1 is a schematic block diagram illustrating a functional configuration of a radiation treatment system of an embodiment of the present invention.

FIG. 1 is a schematic block diagram illustrating a functional configuration of a radiation treatment system of the embodiment of the present invention. In FIG. 1, a radiation treatment system 1 includes a treatment planning apparatus 11, a control device 12 for a radiation treatment apparatus, and a radiation treatment apparatus 13.

The radiation treatment system 1 is a system for performing radiation treatment. Specifically, the radiation treatment system 1 performs irradiation of radiation (radiation for treatment). The radiation for treatment used for irradiation performed by the radiation treatment system 1 may be an electromagnetic wave such as an X-ray or may be a particle beam such as a heavy particle beam and a proton beam.

Particularly, the radiation treatment system 1 performs irradiation of radiation through tracking irradiation. The aforementioned tracking irradiation is a method in which positional information on a particular site moving due to breathing and the like is acquired in real time and the radiation treatment apparatus is controlled such that the radiation treatment apparatus continuously irradiates the particular site with radiation. In addition, the aforementioned particular site is a portion such as a tumor which becomes a target of irradiation of radiation for treatment inside the body of a patient.

The treatment planning apparatus 11 generates a treatment plan for the radiation treatment system 1 to perform irradiation of radiation for treatment. The aforementioned treatment plan is information indicating contents of controlling which the control device 12 for a radiation treatment apparatus performs with respect to the radiation treatment apparatus 13. Specifically, the treatment plan generated by the radiation treatment system 1 indicates a plan how to operate the radiation treatment apparatus 13 and causes the radiation treatment apparatus 13 to perform irradiation of radiation for treatment.

The control device 12 for a radiation treatment apparatus controls the radiation treatment apparatus 13 in accordance with the treatment plan generated by the treatment planning apparatus 11. The control device 12 for a radiation treatment apparatus causes the radiation treatment apparatus 13 to perform irradiation of radiation for treatment through tracking irradiation. For example, the control device 12 for a radiation treatment apparatus is configured to include a computer.

The radiation treatment apparatus 13 executes irradiation of radiation for treatment in accordance with controlling of the control device 12 for a radiation treatment apparatus.

Figure 2:
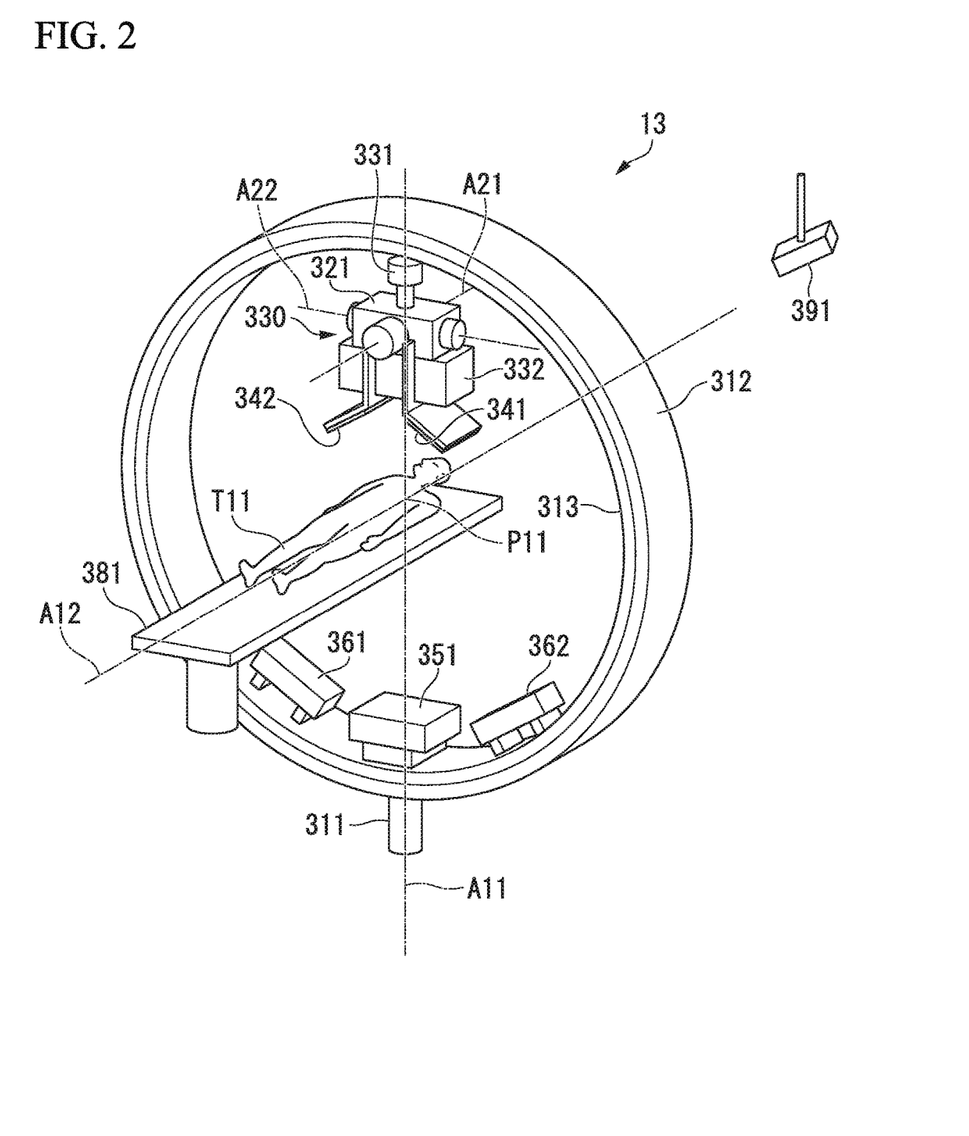
FIG. 2 is a schematic configuration diagram illustrating an apparatus configuration of a radiation treatment apparatus of the embodiment.

FIG. 2 is a schematic configuration diagram illustrating an apparatus configuration of the radiation treatment apparatus 13. In FIG. 2, the radiation treatment apparatus 13 includes a turning drive device 311; an O-ring 312; a traveling gantry 313; an oscillating mechanism (gimbal mechanism) 321; an irradiation unit 330; sensor arrays 351, 361, and 362; and a couch 381. The irradiation unit 330 includes a radiation irradiation device 331, a multi leaf collimator (MLC) 332, radiation sources 341 and 342 for image-capturing, and an infrared (IR) camera 391.

The turning drive device 311 causes the O-ring 312 to be supported by a base in a rotatable manner around a rotary axis A11. The turning drive device 311 rotates the O-ring 312 in accordance with controlling of the control device 12 for a radiation treatment apparatus. The rotary axis A11 is an axis in the vertical direction.

The O-ring 312 is formed to have a ring shape around a rotary axis A12. The O-ring 312 supports the traveling gantry 313 in a rotatable manner around the rotary axis A12. The rotary axis A12 is an axis in the longitudinal direction of the couch 381. In addition, the rotary axis A12 is an axis in the horizontal direction (that is, an axis perpendicular to the vertical direction) and is orthogonal to the rotary axis A11 at an isocenter P11. The rotary axis A12 is fixed with respect to the O-ring 312. In other words, the rotary axis A12 rotates around the rotary axis A11 in accordance with rotation of the O-ring 312.

The traveling gantry 313 is formed to have a ring shape around the rotary axis A12. The traveling gantry 313 is disposed inside the O-ring 312 so as to form a concentric circle together with the O-ring 312. The radiation treatment apparatus 13 further includes a traveling drive device (not illustrated), and the traveling gantry 313 rotates around the rotary axis A12 due to power from the traveling drive device.

The traveling gantry 313 itself rotates. Accordingly, the components such as the radiation source 341 for image-capturing, the sensor array 361, the radiation source 342 for image-capturing, and the sensor array 362 installed in the traveling gantry 313 rotate integrally.

The oscillating mechanism 321 is fixed to the inner side of a ring of the traveling gantry 313 and causes the irradiation unit 330 to be supported by the traveling gantry 313. The oscillating mechanism 321 supports the irradiation unit 330 so as to be able to change the orientation of the irradiation unit 330. The oscillating mechanism 321 changes the orientation of the irradiation unit 330 in accordance with controlling of the control device 12 for a radiation treatment apparatus. Specifically, the oscillating mechanism 321 rotates the irradiation unit 330 around a pan axis A21. In addition, the oscillating mechanism 321 rotates the irradiation unit 330 around a tilt axis A22.

The pan axis A21 is an axis parallel to the rotary axis A12 and is fixed to the traveling gantry 313. The oscillating mechanism 321 causes the irradiation unit 330 to perform an oscillating operation side to side with respect to the rotary axis A12 (accordingly, side to side with respect to a patient T11) by rotating the irradiation unit 330 around the pan axis A21.

The tilt axis A22 is an axis orthogonal to the pan axis A21 and is fixed to the traveling gantry 313. The oscillating mechanism 321 causes the irradiation unit 330 to perform an oscillating operation in the direction of the rotary axis A12 (accordingly, vertically with respect to the patient T11) by rotating the irradiation unit 330 around the tilt axis A22.

The irradiation unit 330 is disposed on the inner side of the traveling gantry 313 while being supported by the oscillating mechanism 321. The irradiation unit 330 performs irradiation of radiation for treatment or radiation for image-capturing.

The radiation irradiation device 331 irradiates a lesion site of the patient T11 with radiation for treatment in accordance with controlling of the control device 12 for a radiation treatment apparatus.

The multi leaf collimator 332 blocks a portion or the entirety of radiation for treatment by opening and closing a leaf in accordance with controlling of the control device 12 for a radiation treatment apparatus. Accordingly, the multi leaf collimator 332 adjusts the irradiation field when the patient T11 is irradiated with radiation for treatment. The multi leaf collimator 332 causes the shape of the irradiation field of radiation for treatment to match the shape of the lesion site by blocking a portion of radiation for treatment. In addition, the multi leaf collimator 332 adjusts the irradiation field by blocking a portion or the entirety of radiation for treatment, thereby adjusting intensity of radiation for treatment.

The radiation source 341 for image-capturing irradiates the sensor array 361 with radiation for image-capturing (an X-ray) in accordance with controlling of the control device 12 for a radiation treatment apparatus. The radiation source 342 for image-capturing irradiates the sensor array 362 with radiation for image-capturing in accordance with controlling of the control device 12 for a radiation treatment apparatus. The radiation sources 341 and 342 for image-capturing are fixed to the irradiation unit 330 (for example, a casing of the multi leaf collimator 332) so as to respectively perform irradiation of radiation in orientations orthogonal to each other.

The sensor array 351 is disposed at a position where radiation for treatment from the radiation irradiation device 331 is directed, while being oriented toward the radiation irradiation device 331. The sensor array 351 is fixed to the inner side of the ring of the traveling gantry 313. The sensor array 351 receives radiation for treatment which has been transmitted through the patient T11 and the like, for the purpose of checking the irradiation position and recording the treatment. The aforementioned expression "receiving radiation" denotes a state of being irradiated with radiation.

The sensor array 361 is disposed at a position where radiation for image-capturing from the radiation source 341 for image-capturing is directed, while being oriented toward the radiation source 341 for image-capturing. The sensor array 361 is fixed to the inner side of the ring of the traveling gantry 313. The sensor array 361 receives radiation for image-capturing with which the radiation source 341 for image-capturing has irradiated the patient T11 and the like and which has been transmitted through the patient T11 and the like, for the purpose of particularizing a lesion site position.

When the sensor array 361 receives radiation for image-capturing from the radiation source 341 for image-capturing, a radiation image can be obtained.

The sensor array 362 is disposed at a position where radiation for image-capturing from the radiation source 342 for image-capturing is directed, while being oriented toward the radiation source 342 for image-capturing. The sensor array 362 is fixed to the inner side of the ring of the traveling gantry 313. The sensor array 362 receives radiation for image-capturing with which the radiation source 342 for image-capturing has irradiated the patient T11 and the like and which has been transmitted through the patient T11 and the like, for the purpose of particularizing the lesion site position.

When the sensor array 362 receives radiation for image-capturing from the radiation source 342 for image-capturing, a radiation image can be obtained. Particularly, in accordance with the combination of the radiation source 342 for image-capturing and the sensor array 362, another radiation image can be obtained in a direction different from that of the combination of the radiation source 341 for image-capturing and the sensor array 361.

The couch 381 is for the patient T11 to lie on, thereby supporting the patient T11. The couch 381 is installed such that the longitudinal direction is oriented toward the direction of the rotary axis A12. The couch 381 can move in various directions while causing the longitudinal direction to be oriented toward the direction of the rotary axis A12.

The infrared (IR) camera 391 receives infrared rays and captures an infrared image. Particularly, the infrared camera 361 is installed so as to be oriented toward the patient T11 lying on the couch 381. The infrared camera 361 captures an image of an infrared marker provided on the body surface of the patient T11 in the vicinity of the lesion site, thereby acquiring three-dimensional positional information on the infrared marker in real time. Particularly, in association with time information, the infrared camera 361 acquires the three-dimensional positional information on the infrared marker at the time thereof.

It is possible to apply various types of methods as a method in which the infrared camera 361 acquires the three-dimensional positional information on the infrared marker. For example, the three-dimensional positional information may be acquired by causing the infrared camera 361 to perform irradiation of an infrared ray and calculating the distance to the infrared marker based on the time taken until the reflected light is received. Otherwise, the three-dimensional positional information may be acquired by causing the infrared camera 361 to capture a stereoscopic image (image of stereogram) of the infrared marker and calculating the distance to the infrared marker based on deviation in the image.

Figure 3:
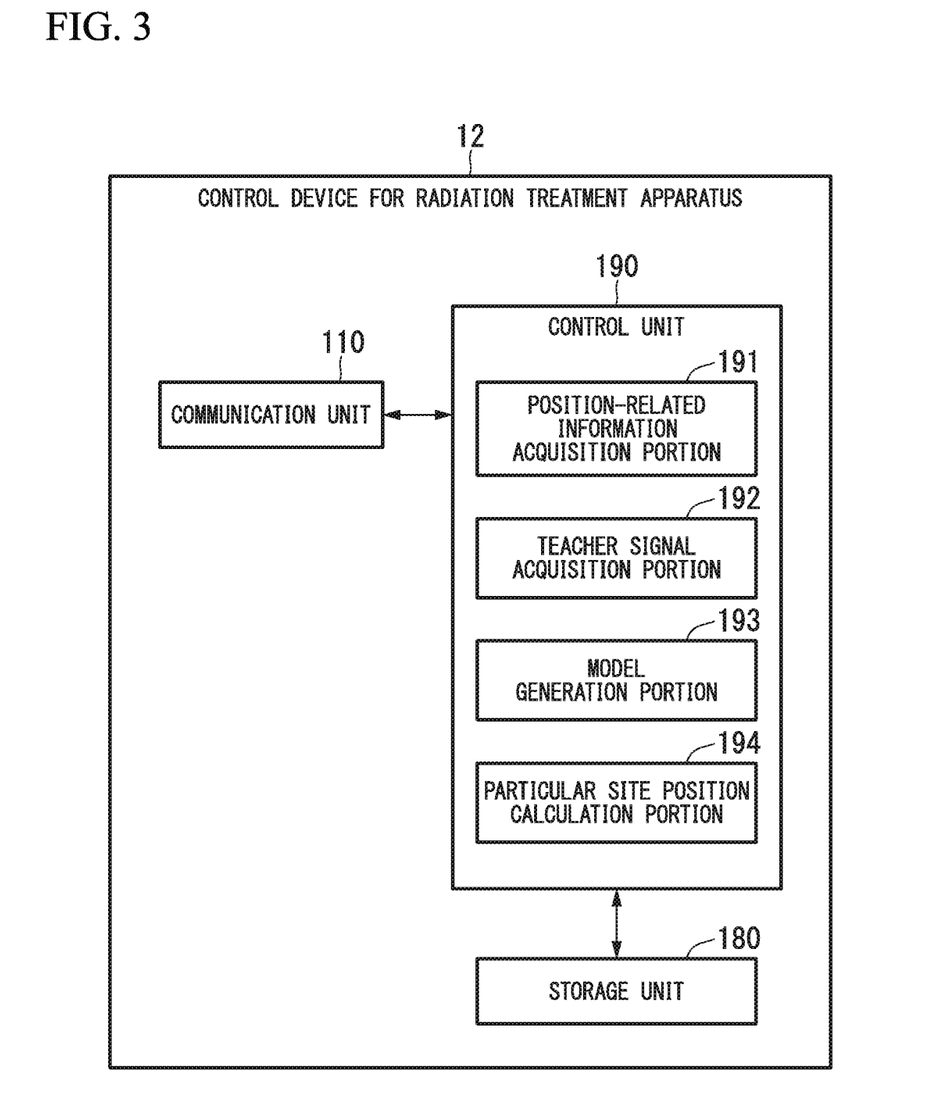
FIG. 3 is a schematic block diagram illustrating a functional configuration of a control device for a radiation treatment apparatus of the embodiment.

FIG. 3 is a schematic block diagram illustrating a functional configuration of the control device 12 for a radiation treatment apparatus. In FIG. 3, the control device 12 for a radiation treatment apparatus includes a communication unit 110, a storage unit 180, and a control unit 190. The control unit 190 includes a position-related information acquisition portion 191, a teacher signal acquisition portion 192, a model generation portion 193, and a particular site position calculation portion 194.

The communication unit 110 communicates with the treatment planning apparatus 11 (FIG. 1) and the radiation treatment apparatus 13. Particularly, the communication unit 110 receives the treatment plan transmitted by the treatment planning apparatus 11. In addition, the communication unit 110 receives the three-dimensional positional information on the infrared marker transmitted by the radiation treatment apparatus 13. Moreover, the communication unit 110 transmits a control signal generated by the control unit 190 with respect to the radiation treatment apparatus 13, to the radiation treatment apparatus 13.

The storage unit 180 stores various types of information. Particularly, a template for the model generation portion 193 to generate a model is stored in the storage unit 180 in advance. In addition, the storage unit 180 stores the model generated by the model generation portion 193.

The storage unit 180 is configured to include a storage device provided in the control device 12 for a radiation treatment apparatus.

The control unit 190 executes various types of functions by controlling each of the components in the control device 12 for a radiation treatment apparatus. Particularly, the control unit 190 generates a control signal with respect to the radiation treatment apparatus 13 based on the treatment plan generated by the treatment planning apparatus 11. In this case, the control unit 190 calculates the three-dimensional positional information on the particular site based on the three-dimensional positional information on the infrared marker acquired by the radiation treatment apparatus 13 (the infrared camera 361), thereby generating a control signal based on the acquired positional information.

For example, execution of the control unit 190 is realized when a central processing unit (CPU) included in the control device 12 for a radiation treatment apparatus reads out a program from the storage device included in the control device 12 for a radiation treatment apparatus.

The position-related information acquisition portion 191 acquires, in real time, the three-dimensional positional information on the infrared marker which is acquired by the infrared camera 361 and is in a form of three-dimensional coordinate information via the communication unit 110.

Here, the position of the infrared marker has a correlationship with the position of the particular site. For example, in a case where the particular site is positioned at the chest or the abdomen of a patient, both the position of the particular site and the position of the infrared marker change due to breathing of the patient. Both the cycle in which the position of the particular site changes and the cycle in which the position of the infrared marker changes are approximately the same as the breathing cycle of the patient. Moreover, as the amount of change in the position of the particular site increases, the amount of change in the position of the infrared marker also tends to increase.

Therefore, the three-dimensional positional information on the infrared marker acquired by the position-related information acquisition portion 191 is used as position-related information. Specifically, the three-dimensional positional information on the infrared marker acquired by the position-related information acquisition portion 191 is used when the particular site position calculation portion 194 calculates the three-dimensional positional information on the particular site.

In this manner, the position-related information acquisition portion 191 acquires the position-related information related to the position of the particular site.

However, in the present embodiment, the position-related information related to the position of the particular site is not limited to the positional information on the infrared marker. Movement of a predetermined portion of a patient may be measured more directly, for example, the control device 12 for a radiation treatment apparatus may measure the height of the abdomen of the patient from the couch in real time, and the result thereof may be used as the position-related information. Otherwise, the control device 12 for a radiation treatment apparatus may measure information such as respiratory volume of a patient indicating a breathing state of the patient, in real time, and the result thereof may be used as the position-related information.

The teacher signal acquisition portion 192 acquires the three-dimensional positional information on the particular site in a form of the three-dimensional coordinate information. For example, the teacher signal acquisition portion 192 acquires the three-dimensional positional information on the particular site based on a two-dimensional perspective image from the combination of the radiation source 341 for image-capturing and the sensor array 361, and another two-dimensional perspective image from the combination of the radiation source 341 for image-capturing and the sensor array 361.

Particularly, in association with the time information, the teacher signal acquisition portion 192 acquires the three-dimensional positional information on the particular site at the time thereof. Accordingly, the three-dimensional positional information on the particular site acquired by the teacher signal acquisition portion 192 is in association with the three-dimensional positional information on the infrared marker acquired at the same time.

The three-dimensional positional information on the particular site acquired by the teacher signal acquisition portion 192 is used as a teacher signal (information indicating correct decision) through which the model generation portion 193 can learn a model indicating the relationship between the position of the infrared marker and the position of the particular site.

Hereinafter, in a case where there is no need to particularly clarify the term, the three-dimensional positional information will be simply referred to as "the positional information".

The model generation portion 193 generates a model outputting the position of the particular site based on the position-related information.

Figure 4:
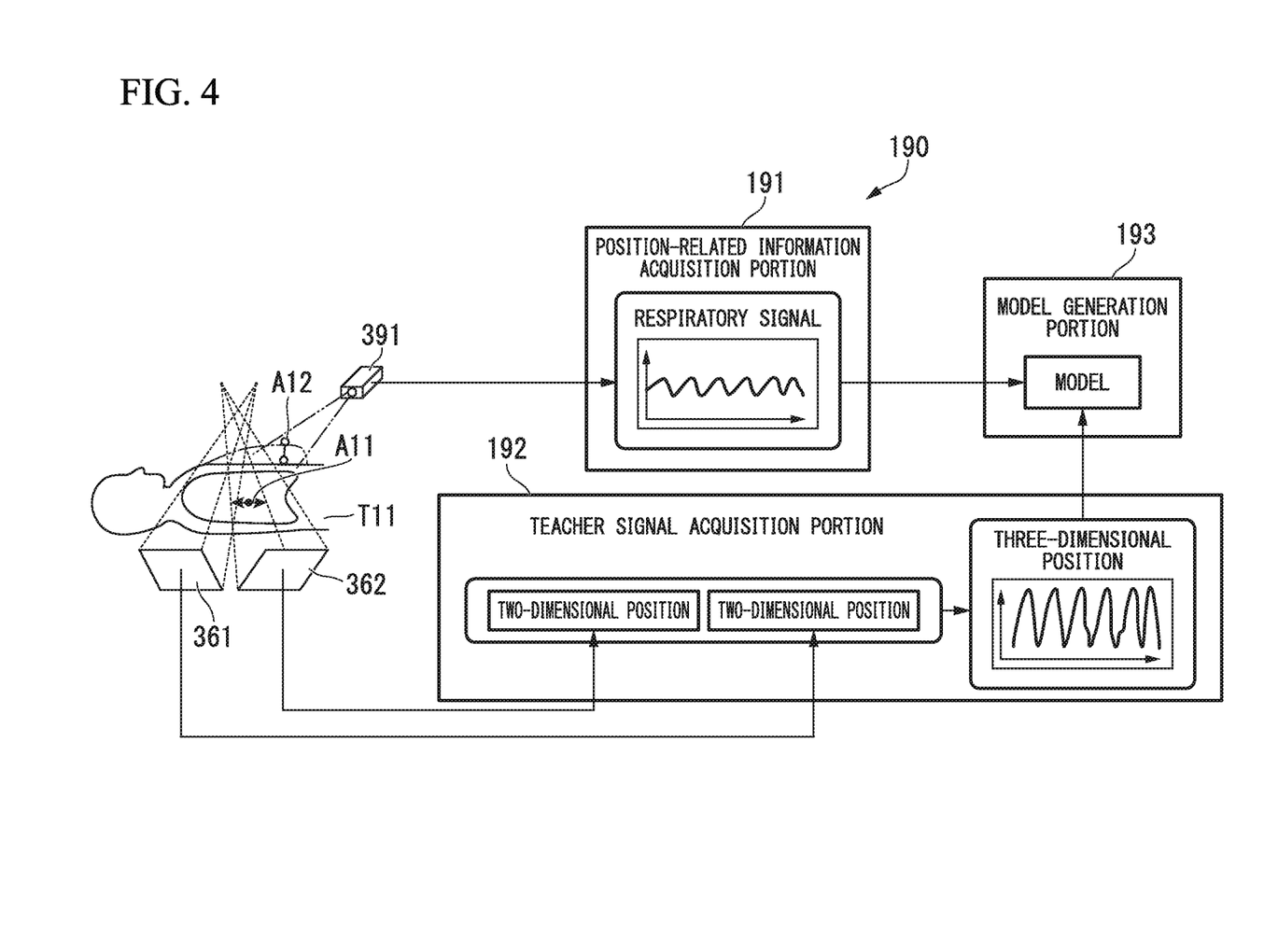
FIG. 4 is an explanatory diagram illustrating an example of a flow of a signal when a model for performing tracking irradiation is generated, in the embodiment.

FIG. 4 is an explanatory diagram illustrating an example of a flow of a signal when a model for performing tracking irradiation is generated. In FIG. 4, the infrared camera 361 acquires the positional information on the infrared marker A12 by capturing an image of the infrared marker A12. The position-related information acquisition portion 191 acquires the positional information on the infrared marker A12 from the infrared camera 361.

In addition, the teacher signal acquisition portion 192 acquires two-dimensional positional information on the particular site A11 based on the two-dimensional perspective image captured when the sensor array 361 receives radiation from the radiation source 341 for image-capturing. Similarly, the teacher signal acquisition portion 192 acquires two-dimensional positional information on the particular site A11 based on the two-dimensional perspective image captured when the sensor array 362 receives radiation from the radiation source 342 for image-capturing. The teacher signal acquisition portion 192 acquires the three-dimensional positional information on the particular site A11 based on the two items of the acquired two-dimensional positional information.

The model generation portion 193 uses the three-dimensional positional information on the infrared marker A12 acquired by the position-related information acquisition portion 191 and the three-dimensional positional information on the particular site A11 acquired by the teacher signal acquisition portion 192, as data for learning, thereby learning the model for performing tracking irradiation. Specifically, through learning, the model generation portion 193 generates the model in which the three-dimensional positional information on the infrared marker A12 is input and the three-dimensional positional information on the particular site A11 is output.

In this manner, the positional information on the infrared marker A12 is used as a respiratory signal. The aforementioned respiratory signal is a signal for correcting deviation caused by breathing and the like, with respect to the positional information on the particular site.

The particular site position calculation portion 194 outputs the positional information on the particular site. Specifically, the particular site position calculation portion 194 applies the position-related information acquired by the position-related information acquisition portion 191 to the model generated by the model generation portion 193, and the particular site position calculation portion 194 calculates the position of the particular site, thereby outputting the result thereof as the positional information.

Figure 5:
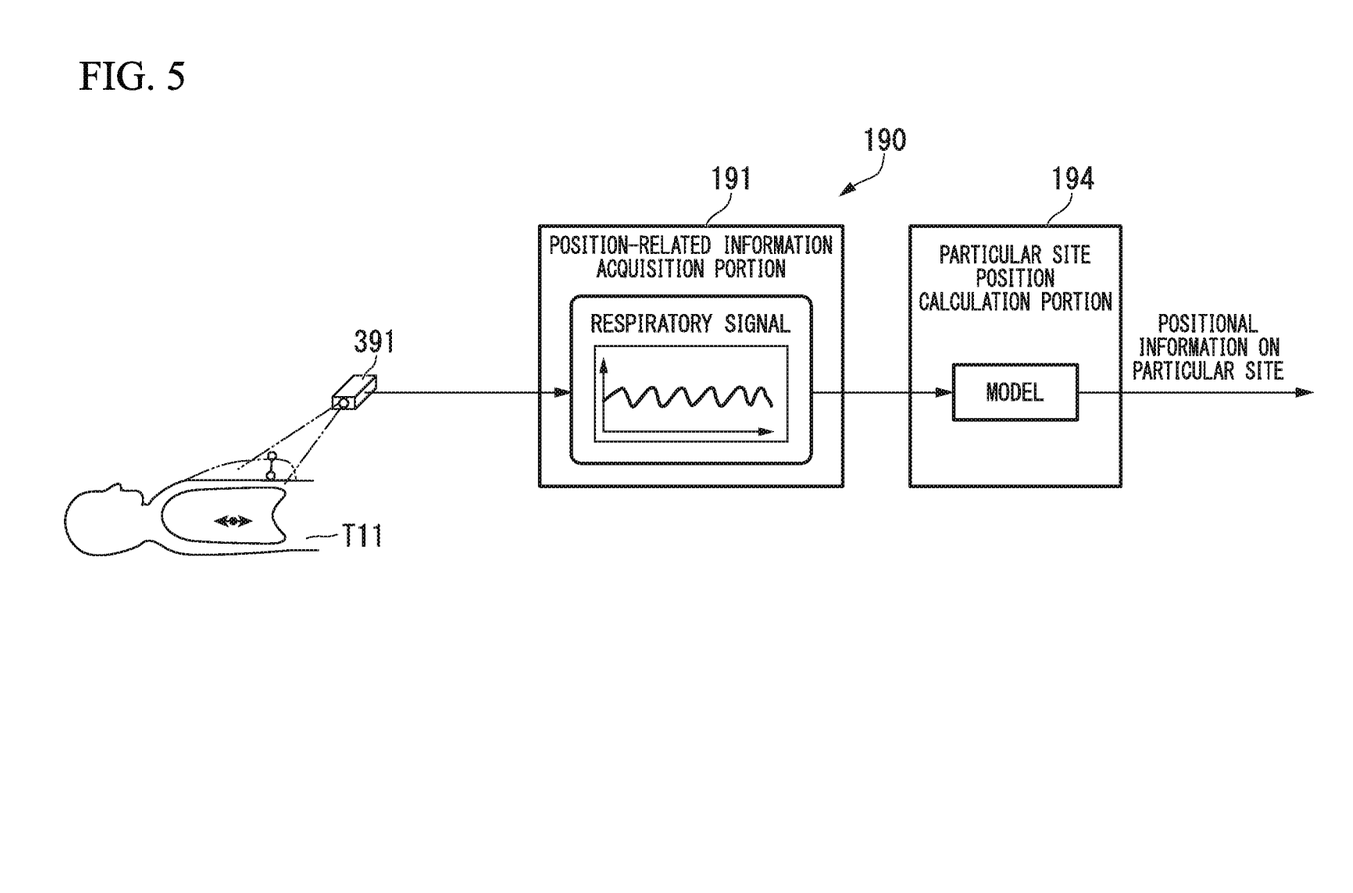
FIG. 5 is an explanatory diagram illustrating another example of the flow of the signal for acquiring positional information on a particular site when tracking irradiation is executed, in the embodiment.

FIG. 5 is an explanatory diagram illustrating another example of the flow of the signal for acquiring positional information on a particular site when tracking irradiation is executed. In FIG. 5, the infrared camera 361 captures an image of the infrared marker A12 and acquires the positional information on the infrared marker A12. The position-related information acquisition portion 191 acquires the positional information on the infrared marker A12 from the infrared camera 361.

The particular site position calculation portion 194 causes the three-dimensional positional information on the infrared marker A12 acquired by the position-related information acquisition portion 191 to be input to the model and outputs the three-dimensional positional information on the particular site A11.

Here, the model generated by the model generation portion 193 (accordingly, the model used by the particular site position calculation portion 194) is provided with a filter regulating an amount of change in the position of the particular site output by the model. In regard to this point, description will be given regarding problems in a case where a model provided with no filter is used, with reference to FIGS. 6 to 9.

Figure 6:
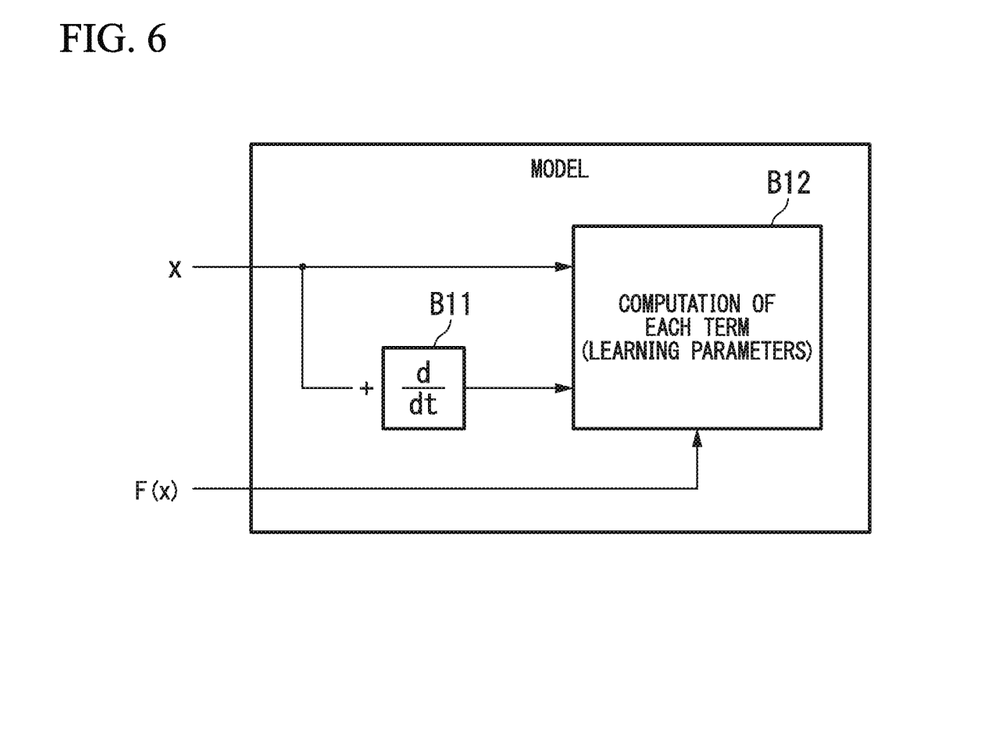
FIG. 6 is a schematic block diagram illustrating an example of a block configuration of a template of a model used by a model generation portion, in the embodiment.

FIG. 6 is a schematic block diagram illustrating an example of a block configuration of the template of the model used by the model generation portion 193. As the template of the model, the model generation portion 193 uses the template having the configuration illustrated in FIG. 6 or the template in which the filter regulating the amount of change in the position of the particular site as an output of the model is further added to the configuration illustrated in FIG. 6.

In FIG. 6, x indicates the three-dimensional positional information on the infrared marker. F(x) indicates the three-dimensional positional information on the particular site.

In addition, a block B11 indicates a block of differentiation. For example, the block B11 is realized by using a differentiation filter (differential filter). A block B12 indicates a block in which computation is performed based on a term using x or differentiation of x.

For example, Equation (1) presents the model based on the template in FIG. 6.

[Math 1]

$$F(x) = a \cdot x^2 + b \cdot x + c \cdot \frac{d}{dt}x + d \cdot \left(\frac{d}{dt}x\right)^2 + e \quad (1)$$

However, "d/dt" indicates first order differentiation. In addition, a, b, c, d, and e respectively indicate constants. Specifically, the constant a indicates a coefficient of a term of square of x. The constant b indicates a coefficient of a term of x. The constant c indicates a coefficient of a term of differentiation of x. The constant d indicates a coefficient of a term of square of differentiation of x. The constant e is configured to be a constant term.

The model generation portion 193 generates a model by determining values of the constants a to e through learning. For example, the model generation portion 193 uses optimization algorithm so as to obtain the values of the constants a to e which minimize an error between the three-dimensional positional information on the particular site calculated based on the three-dimensional positional information on the infrared marker and the teacher signal.

Figure 7:
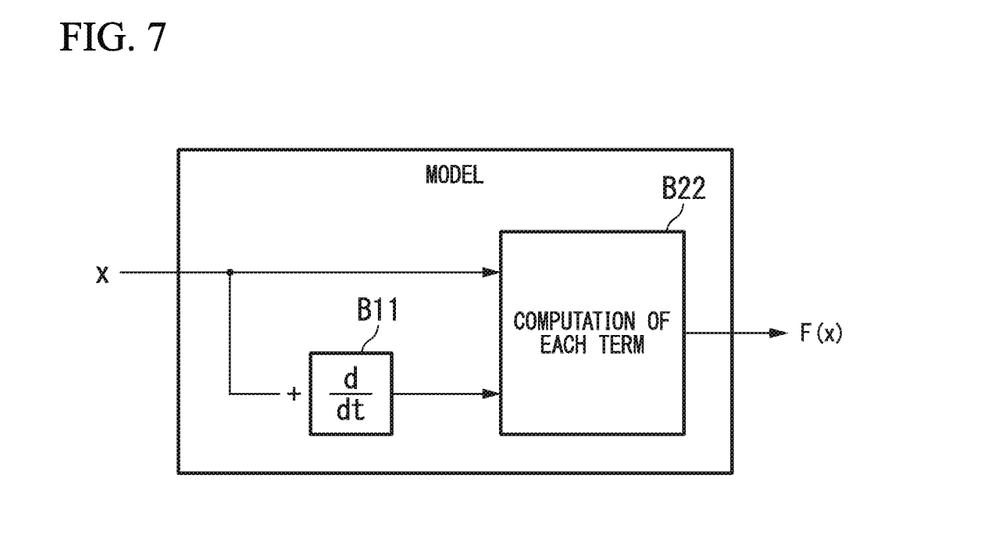
FIG. 7 is a schematic block diagram illustrating an example of the block configuration of the model used by a particular site position calculation portion, in the embodiment.

FIG. 7 is a schematic block diagram illustrating an example of the block configuration of the model used by the particular site position calculation portion 194. FIG. 7 illustrates the block configuration of the model which can be obtained from the template illustrated in FIG. 6. A block B22 indicates a block in which calculation of each term is performed by using the determined values of the constants a to e and the three-dimensional positional information on the particular site is calculated.

Figure 8:
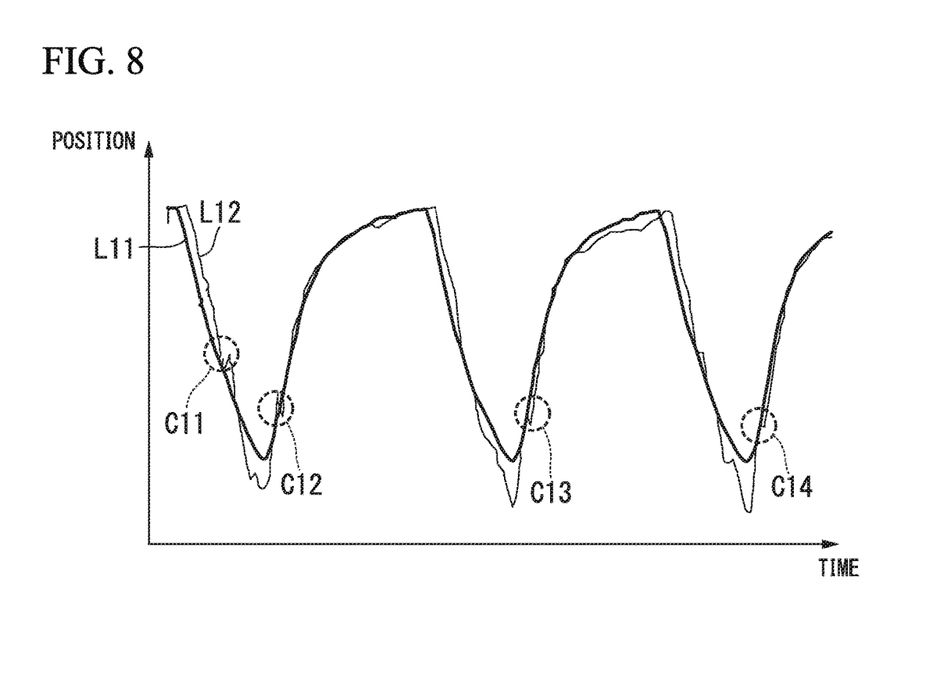
FIG. 8 is a graph illustrating an example of an output of the particular site position calculation portion and teacher data in the embodiment.

FIG. 8 is a graph illustrating an example of an output of the particular site position calculation portion 194 and teacher data. FIG. 8 illustrates a result in which an operation check test of a model which can be obtained through Expression (1) is performed and the output of the particular site position calculation portion 194 and the teacher data are compared with each other.

The horizontal axis in FIG. 8 indicates time. The vertical axis indicates a displacement amount of a position of a patient in the head-foot direction (the longitudinal direction of the couch) from a reference position. A line L11 indicates a teacher signal. A line L12 indicates an output of the particular site position calculation portion 194.

As illustrated in portions indicated by circles C11 to C14 in the line L12, some sudden changes which do not occur in the teacher data can be seen in the output of the particular site position calculation portion 194.

Such sudden changes are not preferable in that an error with respect to the actual position of the particular site indicated in the teacher data becomes significant. In addition, based on the sudden changes thereof, when the control device 12 for a radiation treatment apparatus is intended to cause the radiation treatment apparatus 13 (particularly, the oscillating mechanism 321 or the multi leaf collimator 332) to perform an operation beyond the performance of the radiation treatment apparatus 13, an error occurs and irradiation of radiation is suspended.

Figure 9:
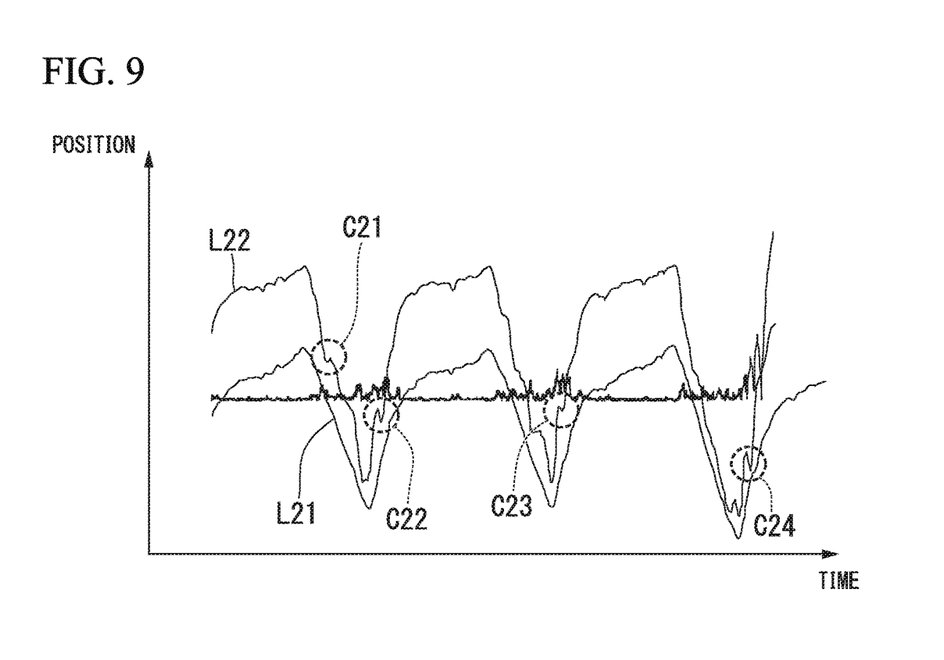
FIG. 9 is a graph illustrating an example of another output of the particular site position calculation portion and a position of an infrared marker in the embodiment.

FIG. 9 is a graph illustrating an example of another output of the particular site position calculation portion 194 and a position of the infrared marker. The inventor of this description has compared the output of the particular site position calculation portion 194 and the position of the infrared marker in order to examine the cause of the sudden changes exemplified in FIG. 8.

The horizontal axis in FIG. 9 indicates time. Regarding a line L21 and a line L22, the vertical axis indicates a displacement amount of a position of a patient in the head-foot direction (the longitudinal direction of the couch) from the reference position. Otherwise, regarding a line L23, the vertical axis indicates a distance. The line L21 indicates the position of the infrared marker. The line L22 indicates the output of the particular site position calculation portion 194. The line L23 indicates the distance between a beam axis and the target.

As illustrated in portions indicated by circles C21 to C24 in the line L22, similar to the case in FIG. 8, sudden changes can be seen. Meanwhile, no sudden change corresponding to the sudden change thereof occurs in the position of the infrared marker indicated by the line L21.

Accordingly, it is considered that the sudden changes in the output of the particular site position calculation portion 194 exemplified in FIGS. 8 and 9 are errors which have occurred during a process of calculation performed by using the model and, for example, which are caused by the amount of change in the term of square of differentiation of x in Expression (1) "d·((d/dt)x)2" which becomes greater than the actual amount of change in the particular site.

In addition, without being limited to a case where an error occurs during the process of calculation performed by using the model, there is also a possibility that the output of the particular site position calculation portion 194 suddenly changes in a case where noise is mixed into the signal used by the control device 12 for a radiation treatment apparatus. For example, in a case where noise is mixed into the positional information on the infrared marker acquired by the position-related information acquisition portion 191, there is a possibility that the output of the particular site position calculation portion 194 suddenly changes.

In order to solve the sudden changes in the output of the particular site position calculation portion 194, it is possible to consider that the amount of change in the output of the particular site position calculation portion 194 is regulated by using a low pass filter. However, when the amount of change in the output of the particular site position calculation portion 194 is simply regulated, there is a possibility that an error becomes significant in a portion other than the portions of the sudden changes.

Figure 10:
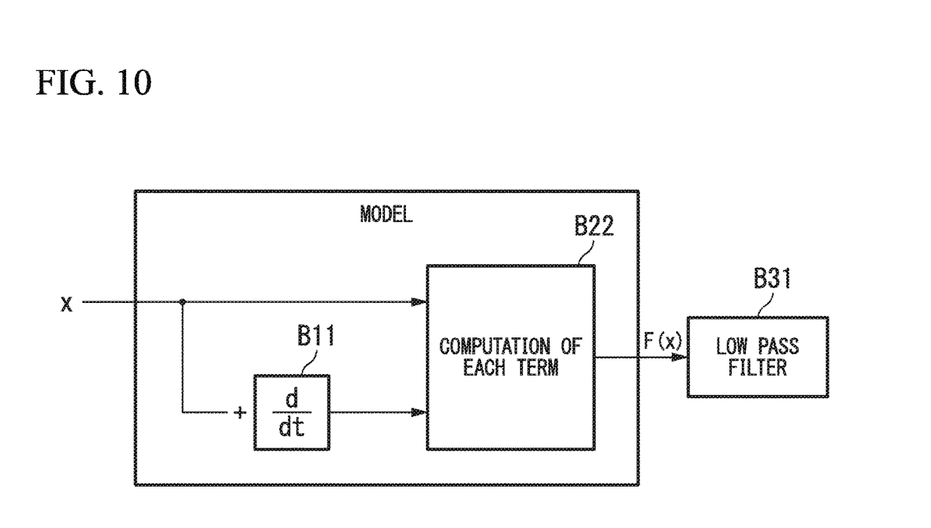
FIG. 10 is a schematic block diagram illustrating an example in which a low pass filter with respect to an output of the model is provided, in the embodiment.

FIG. 10 is a schematic block diagram illustrating an example in which the low pass filter with respect to an output of the model is provided. As illustrated in FIG. 10, when a block B31 of the low pass filter is provided and the amount of change in the output of the particular site position calculation portion 194 is regulated, it is possible to prevent the sudden changes in the output of the particular site position calculation portion 194 from occurring during the process of calculation performed by using the model. The low pass filter indicated in the block B31 corresponds to an example of a filter regulating the amount of change in the output of the particular site position calculation portion 194.

However, due to the low pass filter, it is possible to prevent the change in the output of the particular site position calculation portion 194 caused by displacement of the infrared marker. As a result thereof, there is a possibility that an error of the output of the particular site position calculation portion 194 with respect to the actual position of the particular site becomes significant.

Figure 11:
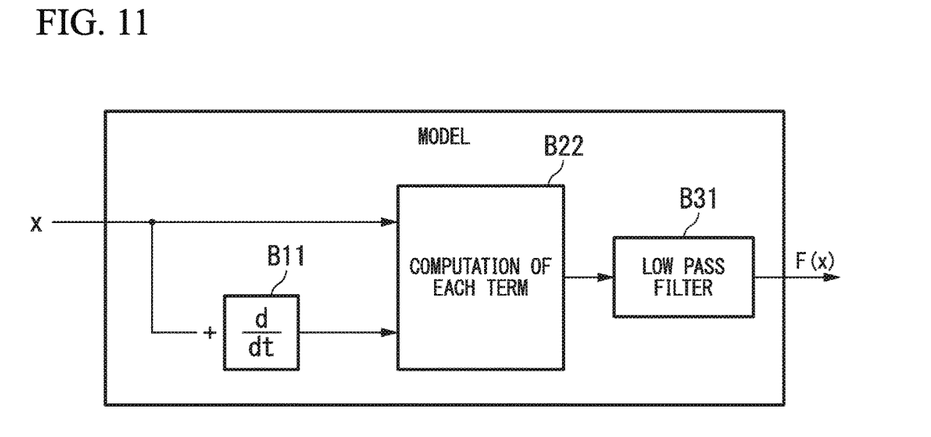
FIG. 11 is a schematic block diagram illustrating a first example in which the low pass filter is provided in the model, in the embodiment.

FIG. 11 is a schematic block diagram illustrating a first example in which the low pass filter is provided in the model. In the example of FIG. 11 being different from the example of FIG. 10, the low pass filter is provided in the model. In order to generate the model, the model generation portion 193 uses the template in which the low pass filter is provided in the model. In other words, the model generation portion 193 sets the parameters of the model template provided with the filter regulating the amount of change in the output of the particular site position calculation portion 194, thereby generating the model provided with the filter.

In this manner, by using the template provided with the low pass filter, the model generation portion 193 sets the parameters so as to minimize an error between an output after passing through the low pass filter and the teacher signal. Accordingly, it is expected that an error between the output of the particular site position calculation portion 194 and the actual position of the particular site becomes relatively small.

Figure 12:
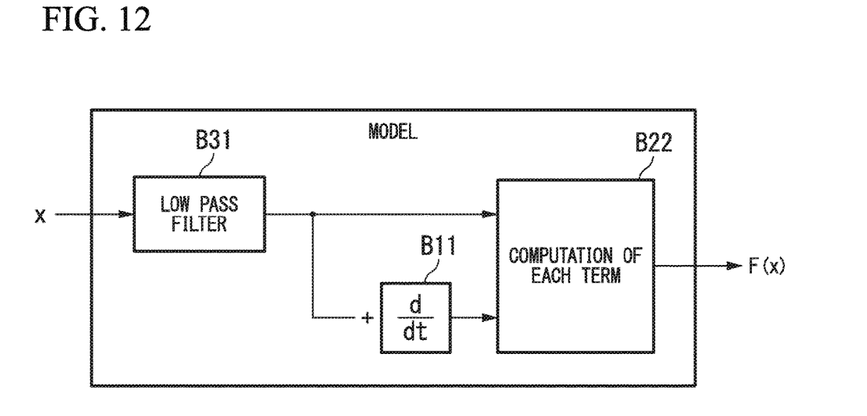
FIG. 12 is a schematic block diagram illustrating a second example in which the low pass filter is provided in the model, in the embodiment.

FIG. 12 is a schematic block diagram illustrating a second example in which the low pass filter is provided in the model. In the example of FIG. 12 being different from the example of FIG. 11, the block B31 of the low pass filter is provided on an entrance side in the model.

Otherwise, the low pass filter can be inserted into a position different from those in the example of FIG. 11 and the example of FIG. 12. For example, in place of the position of the block B31 in FIG. 12, the block B31 may be provided on the differentiation side in the inputs (between the block B11 and the block B22 in FIG. 12). Otherwise, in place of the position of the block B31 in FIG. 12, the block B31 may be provided inside the block B22. For example, the low pass filter may be provided with respect to an input to any one of the terms in Expression (1) or with respect to an output to any one of the terms therein.

Moreover, the low pass filters may be provided in a plurality of portions in the model.

Here, the model generation portion 193 may generate a plurality of the models in each of which the filter is provided at a position different from that in each of the others and may select any one of the models.

For example, the model generation portion 193 sets the parameters of the template having the low pass filter on the entrance side (position illustrated in FIG. 12) in the model, based on the data for learning, thereby generating the model having the low pass filter on the entrance side in the model. In addition, the model generation portion 193 sets the parameters of the template having the low pass filter on the differentiation side in the inputs (between the block B11 and the block B22 in FIG. 12), based on the data for learning, thereby generating the model having the low pass filter on the differentiation side in the inputs.

The model generation portion 193 selects the model in which an error between the output and the teacher signal is evaluated to be relatively small, among the plurality (for example, two) of generated models. Various types of evaluation methods can be applied when evaluating the magnitude of an error by the model generation portion 193. For example, the model generation portion 193 may select the model in which the average value of the magnitude of errors is minimized Otherwise, the model generation portion 193 may select the model in which x+2σ (x indicates the average of errors, and σ indicates standard deviation of an error) is minimized.

The particular site position calculation portion 194 calculates the position of the particular site based on the three-dimensional positional information on the infrared marker acquired by the position-related information acquisition portion 191, by using the model selected by the model generation portion 193, thereby outputting the result thereof.

The model generated by the model generation portion 193 may include a model which is not provided with the filter regulating the amount of change in the position of the particular site output by the model.

As described above, the model generation portion 193 generates the model provided with the filter regulating the amount of change in the position of the particular site output by the model.

Accordingly, the position of the particular site output by the model can be prevented from suddenly changing due to an error occurring during the process of calculation performed by using the model or noise mixed into the signal used by the control device 12 for a radiation treatment apparatus. Accordingly, an error between the output of the model and the actual position of the particular site caused by the sudden change can be prevented from increasing. In addition, it is possible to prevent an error occurring when the control device 12 for a radiation treatment apparatus performs controlling beyond the performance of the radiation treatment apparatus 13, based on the sudden change.

In addition, the model generation portion 193 generates the plurality of models in each of which the filter regulating the amount of change in the position of the particular site output by the model is provided at a position different from that in each of the others. The model generation portion 193 selects any one of the generated models. The particular site position calculation portion 194 calculates the position of the particular site by using the model selected by the model generation portion 193, thereby outputting the result thereof.

Accordingly, the particular site position calculation portion 194 can calculate the positional information on the particular site by using the model provided with the filter at a more suitable position, thereby being able to output the result thereof. Accordingly, it is possible to further reduce an error between the position of the particular site output by the particular site position calculation portion 194 and the actual position of the particular site.

In addition, the model generation portion 193 sets the parameters of the model template provided with the filter regulating the amount of change in the position of the particular site output by the model, thereby generating the model provided with the filter.

Accordingly, the model generation portion 193 can evaluate the output of the model including the influence of the filter and can generate the model having a smaller error between the output and the actual position of the particular site.

A program which realizes the entirety or a portion of the function of the control unit 190 may be recorded in a computer readable recording medium, and processing of each component may be performed by causing a computer system to read and execute the program recorded in the recording medium. The aforementioned "computer system" includes OS and hardware such as peripherals.

In addition, in a case where the WWW system is utilized, "the computer system" is considered to include a homepage-provided environment (or homepage displaying environment).

In addition, the aforementioned "computer readable recording medium" includes a portable medium such as a flexible disk, an magneto-optical disk, ROM, and CD-ROM; and a storage medium such as a hard disk built in the computer system. Moreover, "the computer readable recording medium" includes a medium such as a communication cable in a case where a program is transmitted via a network such as the internet, and a communication channel such as a telephone line, dynamically retaining a program for a short period of time. "The computer readable recording medium" also includes a medium such as a volatile memory in the computer system serving as a server or a client in a case thereof, retaining a program for a certain period of time. In addition, the program may be a program which realizes a portion of the above-described function. Moreover, the program may be a program which can be realized by combining the above-described function with the program which is already recorded in the computer system.

Hereinbefore, the embodiment of the present invention has been described in detail with reference to the drawings. However, the specified configuration is not limited to the embodiment, and a design change and the like are included without departing from the gist and the scope of the invention.

INDUSTRIAL APPLICABILITY

The present invention relates to a control device for a radiation irradiation device including a position-related information acquisition portion that acquires position-related information related to a position of a particular site; a model generation portion that generates a model outputting the position of the particular site based on the position-related information; and a particular site position calculation portion that outputs the position of the particular site based on the position-related information acquired by the position-related information acquisition portion, by using the model generated by the model generation portion. The model generated by the model generation portion is provided with a filter regulating an amount of change in the position of the particular site output by the model.

According to the control device for a radiation treatment apparatus, it is possible to acquire positional information on the particular site with highly improved accuracy.

The invention claimed is:

1. A control device for a radiation irradiation device, the control device comprising:
   a position-related information acquisition portion that acquires position-related information related to a position of a particular site, wherein the position-related information acquisition portion is constructed at least in part of at least one hardware processor and at least one memory;
   a model generation portion that generates a model to determine the position of the particular site based on the position-related information, wherein the model generation portion is constructed at least in part of the at least one hardware processor and the at least one memory; and
   a particular site position calculation portion that outputs the position of the particular site based on the position-related information acquired by the position-related information acquisition portion, by using the model generated by the model generation portion, wherein the particular site position calculation portion is constructed at least in part of the at least one hardware processor and the at least one memory, wherein the model generated by the model generation portion is provided with a filter to regulate an amount of change in the position which represents a real-time position of the particular site, output by the model, and the model generation portion sets parameters of a model template provided with the filter so as to minimize an error between an output after passing through the filter and a teacher signal indicating a correct decision of the position of the particular site, to generate the model provided with the filter.

2. The control device for a radiation irradiation device according to claim 1, wherein the model generation portion generates a plurality of models in each of which the filter is provided at a position different from that in each of the others, and selects any one of the models, and wherein the particular site calculation portion outputs the position of the particular site based on the position-related information acquired by the position-related information acquisition portion, by using the model selected by the model generation portion.

3. The control device for a radiation irradiation device according to claim 1, wherein the filter is a low pass filter.

4. A control method for controlling a radiation treatment apparatus by a control device, the control method comprising:

a position-related information acquisition operation acquiring position-related information related to a position of a particular site;

a model generation operation generating a model outputting the position of the particular site based on the position-related information; and a particular site position calculation operation outputting the position of the particular site based on the position-related information acquired in the position-related information acquisition operation, by using the model generated in the model generation operation, wherein the model generated in the model generation operation is provided with a filter regulating an amount of change in the position which represents a real-time position of the particular site, output by the model; and in the model generation operation, parameters of a model template provided with the filter are set so as to minimize an error between an output after passing through the filter and a teacher signal indicating a correct decision of the position of the particular site, to generate the model provided with the filter.

5. The control method for a radiation irradiation device according to claim 4, wherein the filter is a low pass filter.

6. A program embodied on a non-transitory computer-readable medium, where the program causes a computer including a control device for a radiation treatment apparatus to execute:

a position-related information acquisition operation acquiring position-related information related to a position of a particular site;

a model generation operation generating a model outputting the position of the particular site based on the position-related information; and a particular site position calculation operation outputting the position of the particular site based on the position-related information acquired in the position-related information acquisition operation, by using the model generated in the model generation operation, wherein, in the model generation operation, parameters of a model template provided with a filter are set so as to minimize an error between an output after passing through the filter and a teacher signal indicating a correct decision of the position of the particular site, the filter regulating an amount of change in the position which represents a real-time position of the particular site, output by the model.

7. The program according to claim 6, wherein the filter is a low pass filter.

* * * * *